US009848766B2

(12) United States Patent
Okamoto et al.

(10) Patent No.: US 9,848,766 B2
(45) Date of Patent: Dec. 26, 2017

(54) ANTERIOR EYE THREE-DIMENSIONAL IMAGE PROCESSING APPARATUS AND METHOD OF ANTERIOR EYE THREE-DIMENSIONAL IMAGE PROCESSING

(71) Applicant: Tomey Corporation, Nagoya-shi (JP)

(72) Inventors: Keiichiro Okamoto, Nagoya (JP); Risa Higashita, Nagoya (JP)

(73) Assignee: Tomey Corporation, Nagoya-shi (JP)

( * ) Notice: Subject to any disclaimer, the term of this patent is extended or adjusted under 35 U.S.C. 154(b) by 0 days.

(21) Appl. No.: 15/349,356

(22) Filed: Nov. 11, 2016

(65) Prior Publication Data

US 2017/0135569 A1 May 18, 2017

(30) Foreign Application Priority Data

Nov. 17, 2015 (JP) ................. 2015-224339

(51) Int. Cl.
*A61B 3/14* (2006.01)
*A61B 3/00* (2006.01)
*A61B 3/10* (2006.01)
*A61B 3/117* (2006.01)

(52) U.S. Cl.
CPC ............ *A61B 3/0025* (2013.01); *A61B 3/102* (2013.01); *A61B 3/117* (2013.01)

(58) Field of Classification Search
USPC ............................... 351/200–246
See application file for complete search history.

(56) References Cited

U.S. PATENT DOCUMENTS

| 8,967,810 B1 | 3/2015 | Prager et al. |
| 9,060,717 B2 | 6/2015 | Bailey et al. |
| 9,265,411 B2 | 2/2016 | Chen et al. |

(Continued)

FOREIGN PATENT DOCUMENTS

| JP | 2015-066083 A | 4/2015 |
| JP | 2015-066084 A | 4/2015 |

OTHER PUBLICATIONS

Koichi Mishima, "Clinical Use of Anterior Segment OCT in Glaucoma", Journal of the Eye, vol. 28, No. 6, p. 763-768 (2011).

*Primary Examiner* — Mohammed Hasan
(74) *Attorney, Agent, or Firm* — Shumaker Loop & Kendrick, LLP

(57) ABSTRACT

An anterior eye three-dimensional (3D) image processing apparatus performs: identifying first temporary SS positions in each of at least two representative images selected from a plurality of 2D tomographic images constituting an anterior eye 3D image, each first temporary SS position indicating a space coordinate position of a scleral spur of the subjected eye; calculating a reference circle passing through at least three of the first temporary SS positions; identifying second temporary SS positions in each of at least one non-representative image on the calculated reference circle; extracting regions in a predetermined range in each 2D tomographic image, each region being centered at a corresponding one of the identified first or second temporary SS positions; identifying edge lines each of which indicating a tissue boundary that exists in each extracted region; and correcting the identified first or the second temporary SS positions based on the identified edge lines.

8 Claims, 14 Drawing Sheets

(56) References Cited

U.S. PATENT DOCUMENTS

| | | | |
|---|---|---|---|
| 2014/0112562 A1* | 4/2014 | Yamakawa | A61B 3/102 382/131 |
| 2015/0150447 A1 | 6/2015 | Huang et al. | |
| 2016/0074007 A1 | 3/2016 | Fedor | |

* cited by examiner

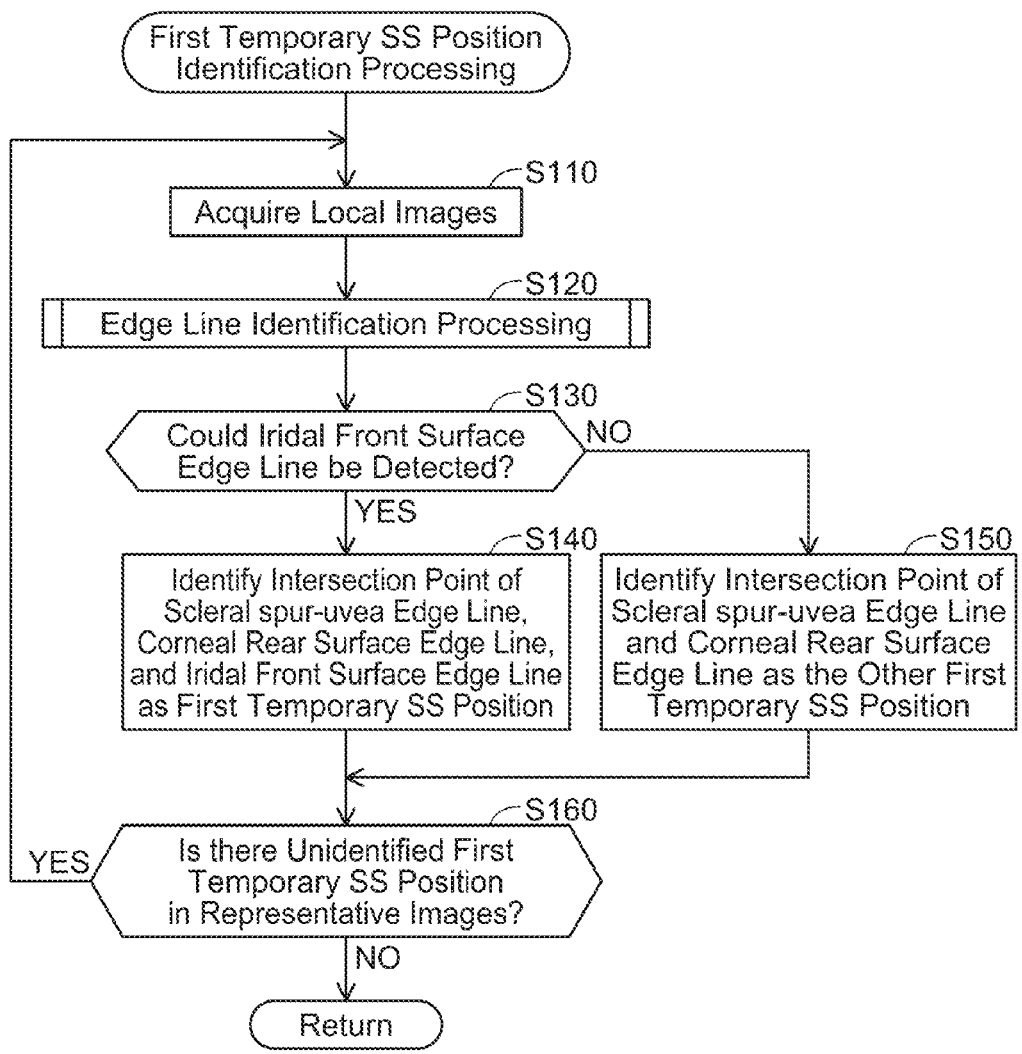

Local Image

Edge Image

Removal of Unnecessary Edge Lines

Scleral spur-uvea Edge Line

ANTERIOR EYE THREE-DIMENSIONAL IMAGE PROCESSING APPARATUS AND METHOD OF ANTERIOR EYE THREE-DIMENSIONAL IMAGE PROCESSING

CROSS-REFERENCE TO RELATED APPLICATION

This application claims priority to Japanese Patent Application No. 2015-224339 filed on Nov. 17, 2015, the contents of which are hereby incorporated by reference into the present application.

TECHNICAL FIELD

The present disclosure relates to an anterior eye three-dimensional image processing apparatus configured to process a three-dimensional image of an anterior eye of a subjected eye and a method thereof.

TECHNICAL BACKGROUND

In recent years, as an examination apparatus used for ophthalmologic examination, an optical coherence tomographic image capturing apparatus (hereinbelow referred to as "anterior eye OCT") which captures a tomographic image of a subject's eyeball (subjected eye) by an optical coherence tomography (OCT) is provided.

Specifically, the anterior eye OCT is used, for example, for glaucomatous examination. A main part of glaucomatous examination is angle analysis of a narrow-angled eye with primary angle closure or primary angle-closure glaucoma and a narrow-angled eye suspected to have primary angle closure or primary angle-closure glaucoma (for example, see Koichi MISHIMA, June, 2011. "*Clinical Use of Anterior Segment OCT in Glaucoma*", Journal of the eye. Vol. 28, No. 6, pp. 763-768).

Generally, in the anterior eye OCT, a two-dimensional tomographic image of one sliced surface is acquired by scanning measurement light one-dimensionally relative to the subjected eye (B-scan), and then a three-dimensional image is obtained by acquiring two-dimensional tomographic images repeatedly while displacing scanning position of the measurement light (in other words, changing a sliced surface) relative to the subjected eye (C-scan).

As a scanning method, there is a method called raster scan as shown in FIG. 4A. In the raster scan, a one-dimensional scan along a scan line extending horizontally (B-scan) is performed repeatedly while moving in a vertical direction to other scan lines (C-scan). Due to this, as shown in FIG. 4B, two-dimensional tomographic images along respective scan lines can be obtained.

Further, there is another method called a radial scan as shown in FIG. 5A. In the radial scan, a one-dimensional scan along a scan line extending radially (B-scan) is performed repeatedly while moving in a circumferential direction to other scan lines (C-scan). Due to this, as shown in FIG. 5B, two-dimensional tomographic images along respective scan lines can be obtained.

In the conventional anterior eye three-dimensional image processing apparatus, an examiner inputted, point by point, a position of a scleral spur (SS position) in each of two-dimensional tomographic images of respective sliced surfaces obtained as mentioned above, as a result of which an angle portion (contact portion of a rear surface of a cornea and a front surface of an iris) which is closed beyond the SS position could be displayed as an iridotrabecular contact (ITC) in a chart form.

A configuration of the conventional anterior eye three-dimensional image processing apparatus required the examiner to input, point by point, the SS position in each two-dimensional tomographic image. Therefore, there was a problem that even if the anterior eye OCT could obtain more than a hundred two-dimensional tomographic images, a large amount of time was taken until a start of creating the chart showing the ITC such that it was difficult to use the apparatus in clinical practice.

In order to address such problem, the present applicant proposed an improved anterior eye three-dimensional image processing apparatus in Japanese Patent Application Publication No. 2015-066084. The anterior eye three-dimensional image processing apparatus disclosed therein is configured to identify SS positions by using at least two representative images among a plurality of two-dimensional tomographic images constituting a three-dimensional image, calculate a reference perfect circle passing through at least three SS positions among the identified SS positions, and then based on the calculated reference perfect circle of the representative images, identify SS positions in non-representative images other than the at least two representative images among the plurality of two-dimensional tomographic images.

In the anterior eye three-dimensional image processing apparatus disclosed in Japanese Patent Application Publication No. 2015-066084 filed earlier by the present applicant, by simply inputting, point by point, the at least three SS positions in the two two-dimensional tomographic images, SS positions in all of the other two-dimensional tomographic images constituting the anterior three-dimensional image can be automatically identified. Due to this, the examiner came to be able to omit the point-by-point input of SS positions, and thus for example, the time taken until the start of creating the chart showing the ITC could be drastically reduced.

Afterwards, as a result of further study and experiments which had been done by the inventors of the present disclosure, an anterior eye three-dimensional image processing apparatus capable of automatically identifying an SS position more accurately than the anterior eye three-dimensional image processing apparatus disclosed in Japanese Patent Application Publication No. 2015-066084 was invented.

SUMMARY

The anterior eye three-dimensional image processing apparatus disclosed herein was invented with a background as mentioned above, and can identify SS positions in two-dimensional tomographic images more stably and accurately than the anterior eye three-dimensional image processing apparatus disclosed in Japanese Patent Application Publication No. 2015-066084. Due to this, it is possible to further reduce a burden of an examiner in an actual place where the anterior eye three-dimensional image processing apparatus is used. The present disclosure aims to provide an improved anterior eye three-dimensional image processing apparatus and a method of an anterior eye three-dimensional image processing.

Aspects of the present disclosure to solve the aforementioned problem will be described hereinbelow. Notably, constituent features employed in the respective aspects described hereinbelow can be employed in any combination possible.

In an aspect of the present disclosure, an anterior eye three-dimensional (3D) image processing apparatus configured to process an anterior eye 3D image of a subjected eye acquired by using an optical coherence tomographic image capturing apparatus is provided. The anterior eye three-dimensional (3D) image processing apparatus comprises a processor, and a memory storing computer-readable instructions therein. The computer-readable instructions, when executed by the processor, cause the anterior eye 3D image processing apparatus to perform: acquiring a plurality of two-dimensional (2D) tomographic images constituting the anterior eye 3D image; identifying first temporary SS positions in each of at least two representative images selected from the plurality of 2D tomographic images, each of the first temporary SS positions indicating a space coordinate position of a scleral spur of the subjected eye; calculating a reference circle passing through at least three of the first temporary SS positions in the anterior eye 3D image; identifying second temporary SS positions in each of at least one non-representative image by using the calculated reference circle on a presumption that the scleral spur is located on the calculated reference circle, the at least one non-representative image being other than the at least two representative images among the plurality of 2D tomographic images; extracting regions in a predetermined range in each of at least one 2D tomographic image selected from the at least two representative images and the at least one non-representative image, in a case where the at least one 2D tomographic image selected from the at least two representative images, each of the regions being centered at a corresponding one of the identified first temporary SS positions, in a case where the at least one 2D tomographic image selected from the at least one non-representative image, each of the regions being centered at a corresponding one of the identified second temporary SS positions; identifying at least one of edge lines each of which indicating a tissue boundary that exists in each of the extracted regions; and correcting the identified first temporary SS positions or the second temporary SS positions based on the identified at least one of the edge lines.

In an aspect of the present disclosure, the identified at least one of the edge lines comprise a scleral spur-uvea edge line indicating a boundary between the scleral spur and an uvea, and a corneal rear surface edge line indicating a rear surface of a cornea.

In an aspect of the present disclosure, when the identified first temporary SS positions or the second temporary SS positions are different from third temporary SS positions which are identified as positions of the scleral spur based on the identified edge lines, the third temporary SS positions are identified as SS positions.

In an aspect of the present disclosure, each of the third temporary SS positions is a position of an intersection point of the scleral spur-uvea edge line indicating the boundary between the scleral spur and the uvea, and the corneal rear surface edge line indicating the rear surface of the cornea.

In an aspect of the present disclosure, each of the third temporary SS positions is a position of a curved point of an edge line which is formed by connecting the scleral spur-uvea edge line indicating the boundary between the scleral spur and the uvea and the corneal rear surface edge line indicating the rear surface of the cornea.

In an aspect of the present disclosure, each of the third temporary SS positions is a position that is identified based on luminance gradient information of the edge line formed by connecting the scleral spur-uvea edge line indicating the boundary between the scleral spur and the uvea and the corneal rear surface edge line indicating the rear surface of the cornea.

In an aspect of the present disclosure, the predetermined range is a range that extends equal to or less than 350 µm from a center of the range that is the corresponding one of the identified first temporary SS positions or the second temporary SS positions.

In an aspect of the present disclosure, a method of processing an anterior eye three-dimensional (3D) image of a subjected eye acquired by using an optical coherence tomographic image capturing apparatus is provided. The method comprises: acquiring a plurality of two-dimensional (2D) tomographic images constituting the anterior eye 3D image; identifying first temporary SS positions in each of at least two representative images selected from the plurality of 2D tomographic images, each of the first temporary SS positions indicating a space coordinate position of a scleral spur of the subjected eye; calculating a reference circle passing through at least three of the first temporary SS positions in the anterior eye 3D image; identifying second temporary SS positions in each of at least one non-representative image by using the calculated reference circle on a presumption that the scleral spur is located on the calculated reference circle, the at least one non-representative image being other than the at least two representative images among the plurality of 2D tomographic images; extracting regions in a predetermined range in each of at least one 2D tomographic image selected from the at least two representative images and the at least one non-representative image, in a case where the at least one 2D tomographic image selected from the at least two representative images, each of the regions being centered at a corresponding one of the identified first temporary SS positions, in a case where the at least one 2D tomographic image selected from the at least one non-representative image, each of the regions being centered at a corresponding one of the identified second temporary SS positions; identifying at least one of edge lines each of which indicating a tissue boundary that exists in each of the extracted regions; and correcting the identified first temporary SS positions or the second temporary SS positions based on the identified at least one of the edge lines.

According to the anterior eye 3D image processing apparatus and the method of processing an anterior eye 3D image, by correcting the identified temporary SS positions based on the reference circle, the temporary SS positions in the 2D tomographic images can be identified stably and accurately. Further, by limiting the range in which the edge line indicating a tissue boundary is detected to the areas in the predetermined range whose centers are the identified temporary SS positions, it is possible to reduce detection of a wrong tissue boundary, and carry out an arithmetic processing for correction of the temporary SS positions at a faster speed.

BRIEF DESCRIPTION OF DRAWINGS

FIG. 8 is a flowchart for explaining a first temporary SS position identification processing performed in the main processing;

DETAILED DESCRIPTION

First Embodiment

An anterior eye optical coherence tomographic image capturing apparatus of a first embodiment is used for ophthalmologic examinations for an anterior eye Ec of a subject's eyeball (subjected eye E) (see FIG. 1) such as an angle analysis, and measurements of a corneal curvature, a distribution of corneal thickness, an anterior chamber depth, and the like. The anterior eye optical coherence tomographic image capturing apparatus obtains a three-dimensional (3D) image by capturing two-dimensional (2D) tomographic images of the anterior eye Ec of the subjected eye E by Optical Coherence Tomography (OCT). Hereinbelow, the anterior eye optical coherence tomographic image capturing apparatus is referred to as "anterior eye OCT 1".

Although not shown, a main body of the anterior eye OCT 1 is supported so as to be movable in an X direction (left-and-right direction), in a Y direction (up-and-down direction), and in a Z direction (front-and-rear direction) relative to a holding table. A chin support and a forehead pad are fixed relative to the holding table on a front face side (subject side) of the main body of the anterior eye OCT 1.

When the subject puts the chin on the chin support and puts the forehead against the forehead pad, the subject's eye (subjected eye E) comes to be positioned in front of an inspection window for capturing images (through which light comes in and goes out) which is provided in a front face of the main body of the anterior eye OCT 1.

Figure 2:
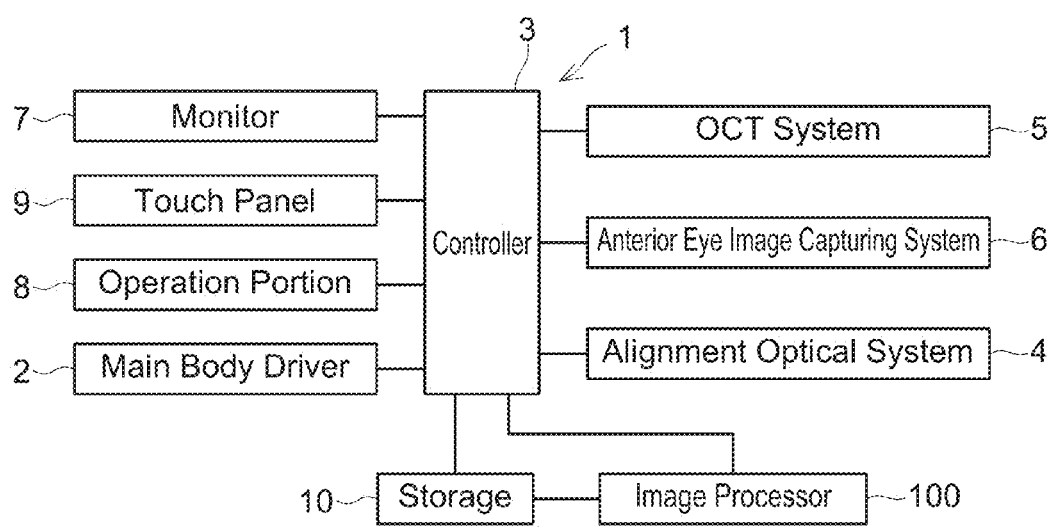
FIG. 2 is a block diagram schematically illustrating an electrical configuration of the anterior eye OCT 1.

As shown in FIG. 2, the anterior eye OCT 1 comprises a main body drive 2 configured to move the main body of the anterior eye OCT 1 relative to the holding table freely in each of the X, Y, and Z directions. This main body drive 2 comprises a well-known configuration including an X-direction movement motor, a Y-direction movement motor, a Z-direction movement motor, and the like, and is controlled by a controller 3.

As shown in FIG. 2, the main body of the anterior eye OCT 1 comprises the controller 3, an alignment optical system 4, an OCT system 5, an anterior eye image capturing system 6, and the like. The controller 3 comprises a microcomputer including a CPU, a memory, and the like and is configured to perform overall control of the anterior eye OCT 1. The OCT system 5 is configured to acquire a 3D image of the anterior eye Ec (hereinbelow referred to as "anterior eye 3D image") constituted of a plurality of 2D tomographic images. The anterior eye image capturing system 6 is configured to capture a front image of the subjected eye E.

Further, the main body of the anterior eye OCT 1 comprises a monitor 7 and an operation portion 8. The monitor 7 is positioned on a rear face side (examiner's side) of the main body of the anterior eye OCT 1 and is configured to display a front image P of the subjected eye E (see FIG. 1) and the like. The operation portion 8 is a boundary for the examiner to perform various kinds of operations. Although not shown, the operation portion 8 may comprise a measurement start switch, a measurement region designating switch, a key board, a mouse, and the like.

Although FIG. 2 shows a touch panel 9 and the operation portion 8 as separate configurations, the touch panel 9 may be included in the operation portion 8. The touch panel 9 is integrally provided with a screen of the monitor 7. A storage 10 and an image processor 100 (a main part of an anterior eye 3D image processing apparatus) are connected to the controller 3.

The storage 10 may be a device capable of storing data in a computer-readable recording medium such as a hard disk, a CD-ROM/RAM, a DVD-ROM/RAM, a semiconductor memory, or the like. The storage 10 stores image data of a captured anterior eye 3D image and the like. The image processor 100 performs an image processing of the stored data of the anterior eye 3D images and the like.

The OCT system 5 is configured to obtain an anterior eye 3D image by OCT. In the present embodiment, Fourier domain (optical frequency sweep) system is employed in which a wavelength scanning light source 11 (see FIG. 1) which performs scans while temporally changing a wavelength is used.

Figure 1:
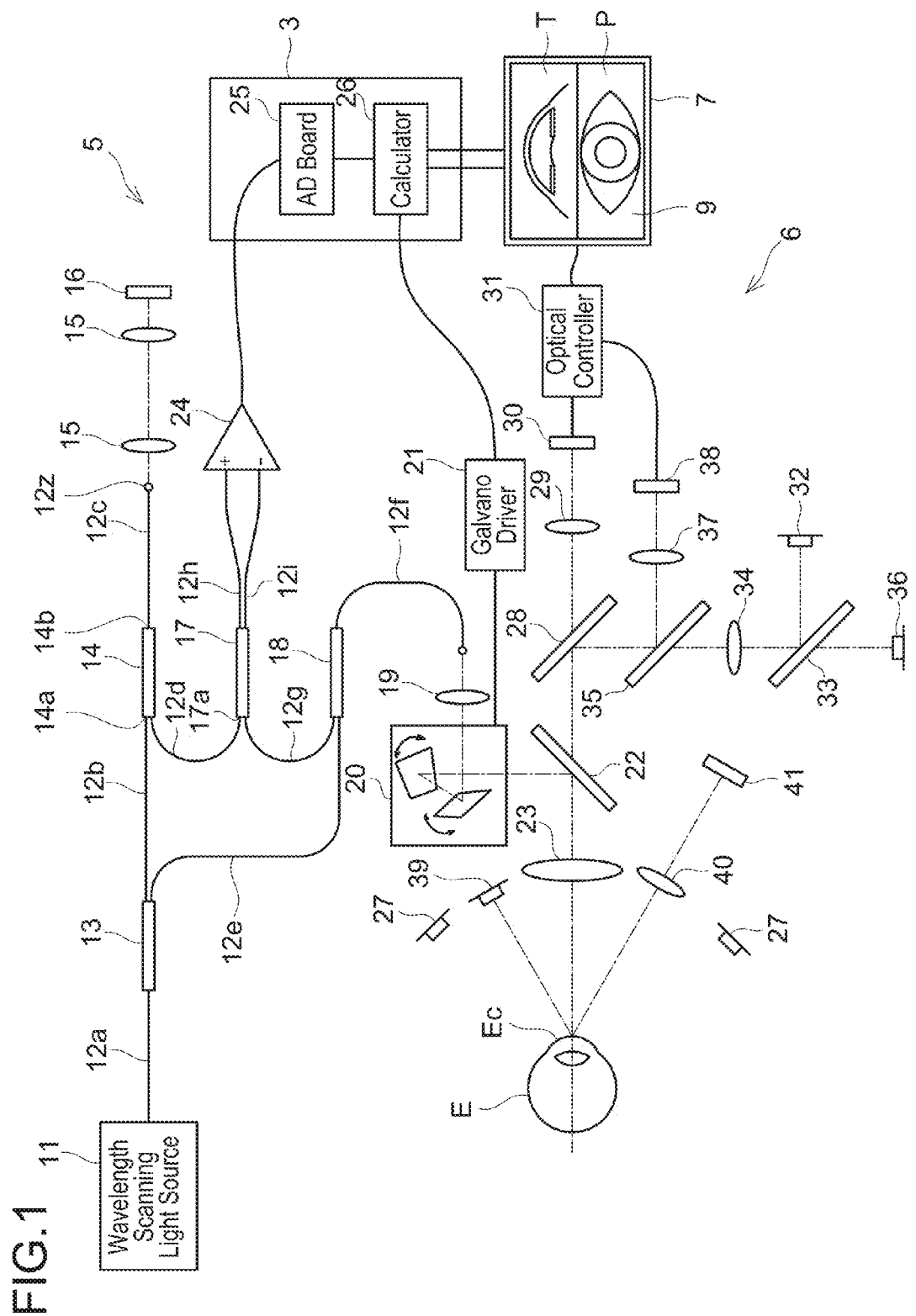
FIG. 1 is a diagram illustrating configurations of optical systems of an anterior eye OCT 1.

For example, as shown in FIG. 1, light outputted from the wavelength scanning light source 11 is inputted to a first fiber coupler 13 through an optical fiber 12a. In the first fiber coupler 13, the light inputted to the first fiber coupler 13 is demultiplexed into reference light and measurement light, for example at a ratio of 1:99, and each light is outputted from the first fiber coupler 13. The reference light is inputted to an input-output portion 14a of a first circulator 14 through an optical fiber 12b, outputted from an input-output portion 14b of the first circulator 14, passes through an optical fiber 12c, is outputted from an end 12z of the optical fiber 12c.

The reference light outputted from the end 12z of the optical fiber 12c passes through a plurality of collimator lenses 15, and then enters a reference minor 16.

The reference light reflected by the reference mirror 16, again, passes through the plurality of the collimator lenses 15, is inputted to the end 12z of the optical fiber 12c, passes through the optical fiber 12c, and is inputted to the input-output portion 14b of the first circulator 14. Then, the reference light inputted to the input-output portion 14b of the first circulator 14 is outputted from the input-output portion 14a of the first circulator 14, passes through an optical fiber 12d and is inputted to a first input portion 17a of a second fiber coupler 17.

Meanwhile, the measurement light outputted from the first fiber coupler 13 is inputted to an input portion of a second circulator 18 through an optical fiber 12e. Further, the measurement light is outputted from an input-output portion of the second circulator 18, passes through an optical fiber 12f, and is outputted from an end of the optical fiber 12f.

The measurement light outputted from the end of the optical fiber 12f passes through a collimator lens 19 and is inputted to a Galvano scanner 20. The Galvano scanner 20 is configured to scan the measurement light and driven by a Galvano driver 21.

The measurement light outputted from the Galvano scanner 20 is reflected at 90 degrees by a hot mirror 22 which reflects light a wavelength of which is on a long-wavelength side and allows light a wavelength of which is on a short-wavelength side to pass therethrough, passes through an objective lens 23, is outputted from the inspection window, and then enters the subjected eye E.

The measurement light which has entered the subjected eye E is reflected at respective structural parts of the anterior eye Ec (a cornea, anterior chamber, iris, crystalline lens, uvea, scleral and the like). The reflected light enters the inspection window, and in an inverse order to the order mentioned above, passes through the objective lens 23, the hot mirror 22, the Galvano scanner 20, and the collimator lens 19, and is inputted to the end of the optical fiber 12f.

The reflected light inputted to the end of the optical fiber 12f passes through the optical fiber 12f, is inputted to the input-output portion of the second circulator 18, is output from an output portion of the second circulator 18, passes through an optical fiber 12g, and then is inputted to a second input portion of the second fiber coupler 17.

In the second fiber coupler 17, the reflected light from the anterior eye Ec that was inputted through the optical fiber 12g and the reference light inputted through the optical fiber 12d are multiplexed, for example at a ratio of 50:50, and a signal thereof passes through an optical fiber 12h and an optical fiber 12i, and is inputted to a detector 24.

In the detector 24, interference of every wavelength is measured. The measured interference signals are inputted to an AD board 25 provided in the controller 3. Further, in a calculator 26 provided in the controller 3, processing such as Fourier transform and the like is performed to the interference signals. Due to this, tomographic images of the anterior eye Ec along scan lines (2D tomographic images) are obtained.

A scanning pattern of the measurement light by the Galvano scanner 20, a direction of the scan lines (B-scan) in other words, is set in the controller 3. That is, the Galvano driver 21 controls the Galvano scanner 20 according to a command signal from the controller 3 (the calculator 26).

Image data of the 2D tomographic images obtained as above is stored in the storage 10. This image data of the 2D tomographic images includes at least information indicating a luminance of each pixel. Further, as shown schematically in FIG. 1, a 2D tomographic image T of the 2D tomographic images can be displayed on the monitor 7.

The anterior eye image capturing system 6 comprises two illumination light sources 27, the objective lens 23, the hot mirror 22, a cold mirror 28, an imaging lens 29, a CCD camera 30, and an optical controller 31. The two illumination light sources 27 are configured to radiate illumination light within a visible light range to a front surface of the subjected eye E.

The light reflected by the subjected eye E is inputted to the CCD camera 30 from the inspection window through the objective lens 23, the hot mirror 22, the cold mirror 28, and the imaging lens 29. Due to this, the front image P of the subjected eye E is captured. The captured front image P is image-processed by the optical controller 31, and then displayed on the monitor 7.

The alignment optical system 4 comprises a vision-fixation lamp optical system, an XY directional position detecting system, and a Z directional position detecting system. The vision-fixation lamp optical system is configured to suppress a movement of the eyeball (subjected eye E) as much as possible by making the subject stare at a vision-fixation lamp. The XY directional position detecting system is configured to detect positions of a corneal apex of the subjected eye E in the X and Y directions (displacements of the corneal apex in the up-and-down direction and the right-and-left direction relative to the main body of the anterior eye OCT 1). The Z directional position detecting system is configured to detect a position of the corneal apex of the subjected eye E in the front-and-rear direction (Z direction).

The vision-fixation lamp optical system comprises a vision-fixation lamp 32, a cold mirror 33, a relay lens 34, a half mirror 35, the cold mirror 28, the hot mirror 22, the objective lens 23, and the like. Light outputted from the vision-fixation lamp 32 (for example, green light) is outputted to the subjected eye E from the inspection window after passing through the cold mirror 33, the relay lens 34, the half mirror 35, the cold mirror 28, the hot minor 22, and the objective lens 23 in this order.

The XY directional position detecting system comprises an XY position detecting light source 36, the cold mirror 33, the relay lens 34, the half minor 35, the cold minor 28, the hot mirror 22, the objective lens 23, an imaging lens 37, a position sensor 38, and the like.

Alignment light for position detection is outputted from the XY position detecting light source 36. The alignment light enters the anterior eye Ec (cornea) of the subjected eye E after passing through the cold mirror 33, the relay lens 34, the half mirror 35, the cold mirror 28, the hot mirror 22, the objective lens 23, and the inspection window.

Since a corneal surface of the subjected eye E has a spherical shape, the alignment light is reflected on the corneal surface so as to form a bright point image on an inner side of the corneal apex of the subjected eye E. The reflected light (bright point) from the corneal surface enters the main body of the anterior eye OCT 1 from the inspection window.

Figure 3A:
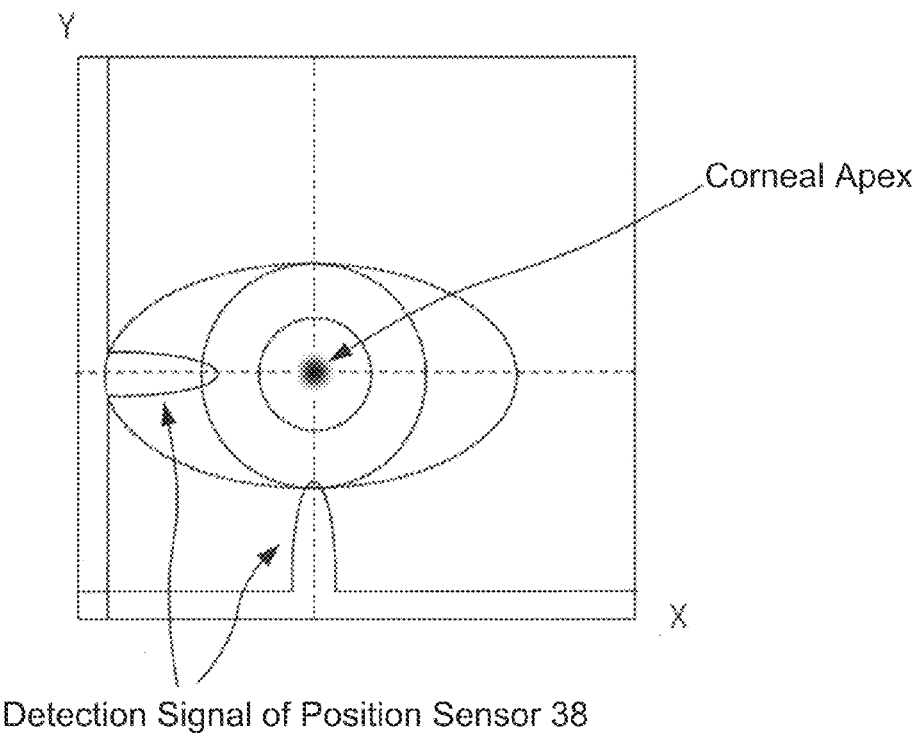
FIG. 3A is a complementary diagram for explanation of an alignment processing performed by a controller.

The reflected light from the corneal apex is inputted to the position sensor 38 after passing through the objective lens 23, the hot mirror 22, the cold mirror 28, the half mirror 35, and the imaging lens 37. A position of the bright point is detected by the position sensor 38. Due to this, the position of the corneal apex (position in the X and Y directions) is detected (see FIG. 3A). The bright point is displayed on the image captured by the CCD camera 30 (the image displayed on the monitor 7) as well.

A detection signal of the position sensor 38 is inputted to the controller 3 (the calculator 26) via the optical controller 31. In the present embodiment, a memory or the storage 10 is provided with a program for realizing a part of functions as the anterior eye 3D image processing apparatus. In the calculator 26 of the controller 3, the CPU performs an alignment processing in accordance with the program.

In the alignment processing, based on the detection signal (detection result) of the position sensor 38, positional displacement amounts ΔX and ΔY of the detected corneal apex (bright point) in the X direction and the Y direction relative to a predetermined (regular) image acquiring position of the corneal apex are found.

The Z directional position detecting system comprises a Z directional position detecting light source 39, an imaging lens 40, and a line sensor 41. The Z directional position detecting light source 39 radiates light for detection (slit light or spot light) to the subjected eye E obliquely relative to the subjected eye E.

Figure 3B:
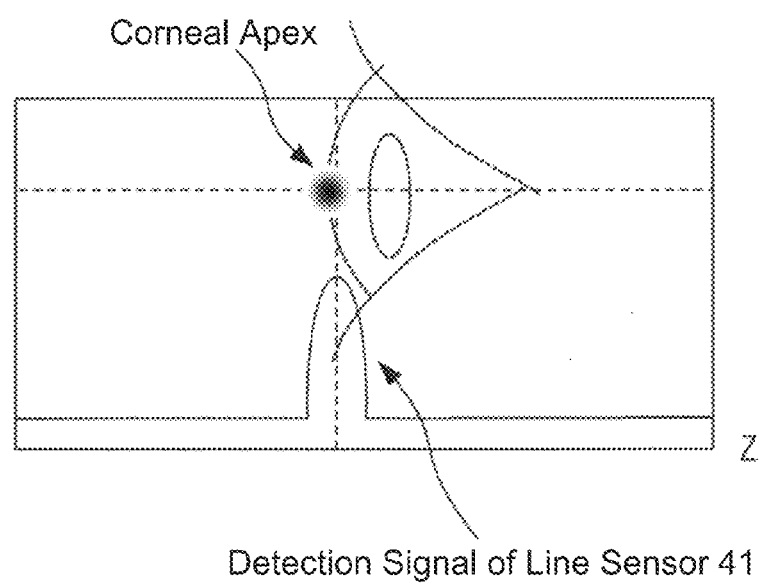
FIG. 3B is a complementary diagram for explanation of the alignment processing performed by the controller.

The light reflected obliquely by the cornea enters the line sensor 41 through the imaging lens 40. Depending on a position of the subjected eye E in the front-and-rear direction (Z direction) relative to the main body of the anterior eye OCT 1, an incident position of the reflected light which enters the line sensor 41 varies. Due to this, the position (distance) of the subjected eye E in the Z direction relative to the main body of the anterior eye OCT 1 is detected (see FIG. 3B).

A detection signal of the line sensor 41 is inputted to the controller 3 (the calculator 26) via the optical controller 31. An appropriate position (distance) of the corneal apex of the subjected eye E in the Z direction relative to the main body of the anterior eye OCT 1 has been predetermined in the calculator 26 of the controller 3. Due to this, in the alignment processing, the calculator 26 of the controller 3 finds a positional displacement amount ΔZ of the detected corneal apex in the Z direction relative to the appropriate position based on the detection signal (detection result) of the line sensor 41.

In the alignment processing, the calculator 26 of the controller 3 stores in the storage 10 the positional displacement amounts ΔX, ΔY of the corneal apex in the X direction and the Y direction detected by the XY directional position detecting system, and the positional displacement amount ΔZ of the corneal apex in the Z direction detected by the Z directional position detecting system as alignment information. In this case, the alignment information is stored in a saving format which can identify the image data of each 2D tomographic image corresponding to the alignment information.

The calculator 26 of the controller 3 acquires a 2D tomographic image of one sliced surface by scanning the measurement light one-dimensionally relative to the subjected eye E (B-scan), and acquires 2D tomographic images repeatedly while displacing scanning position of the measurement light (in other words, changing sliced surfaces) relative to the subjected eye E (C-scan). Then the controller 3 stores in the storage 10 the obtained anterior eye 3D image. Further, the controller 3 stores in the storage 10 the alignment information corresponding to each of the 2D tomographic images which constitute the anterior eye 3D image.

Figure 4A:
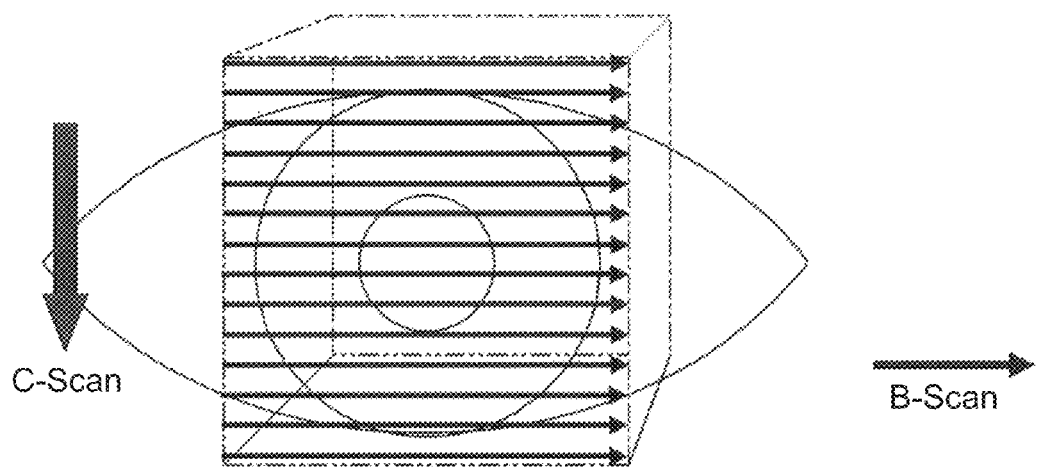
FIG. 4A is a diagram for explaining a raster scan method.
Figure 4B:
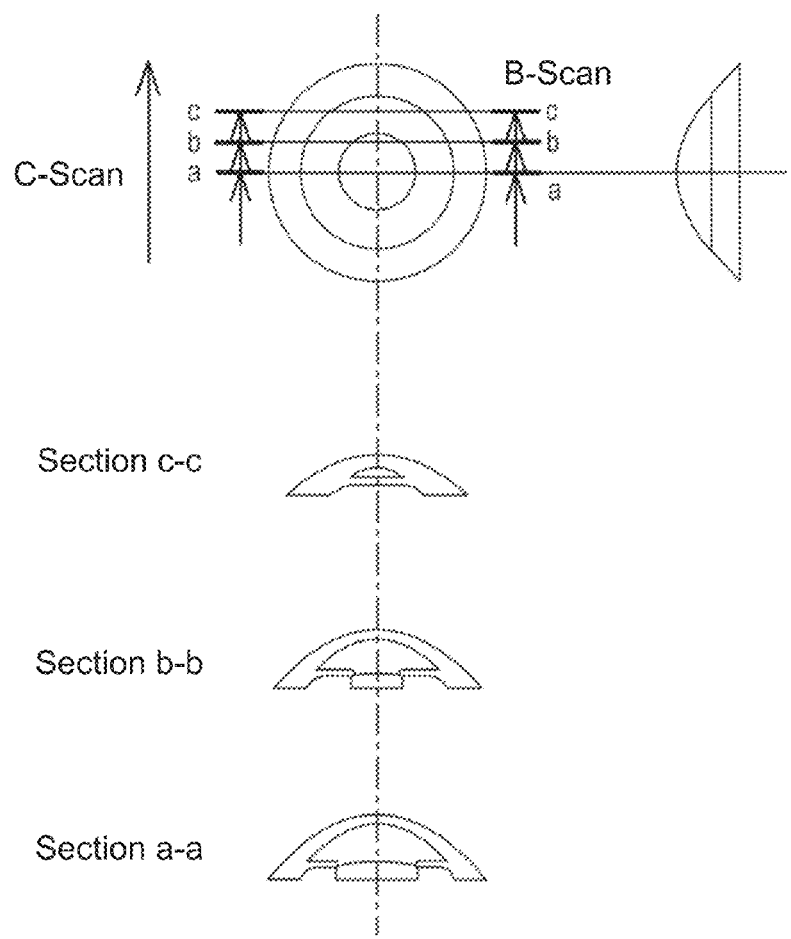
FIG. 4B is a diagram for explaining the raster scan method.
Figure 5A:
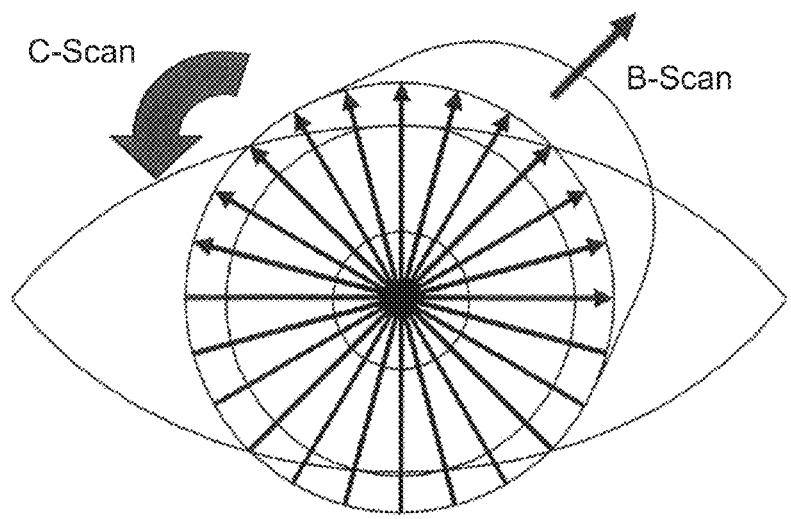
FIG. 5A is a diagram for explaining a radial scan method.
Figure 5B:
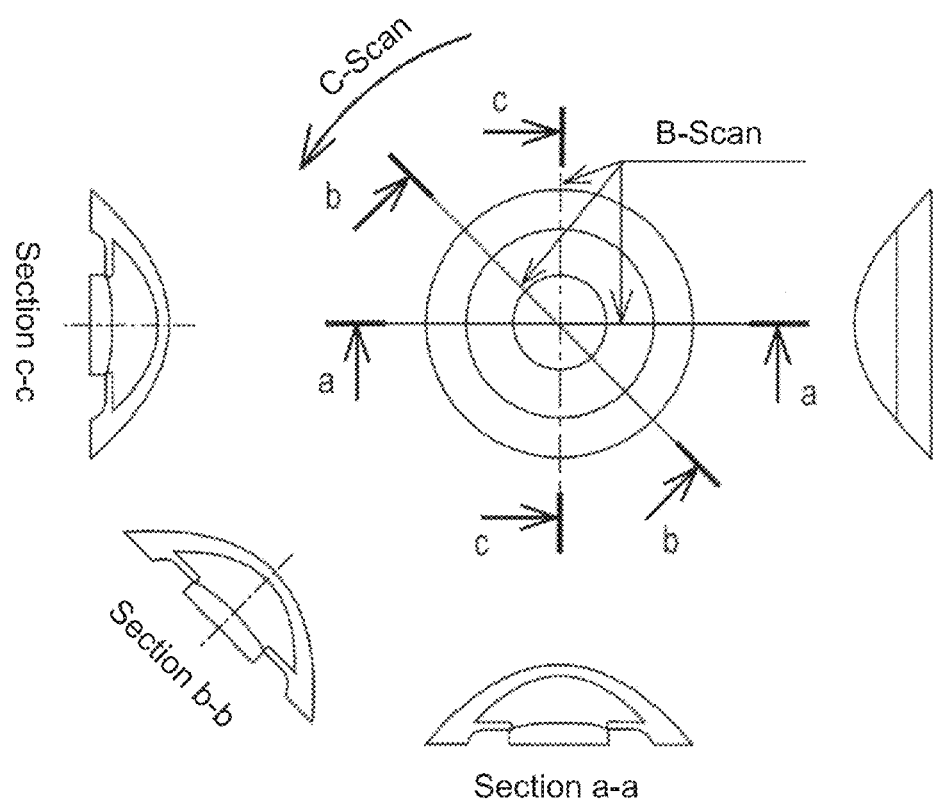
FIG. 5B is a diagram for explaining the radial scan method.

As aforementioned, as a scanning method, there are a method called raster scan as shown in FIGS. 4A, 4B and a method called radial scan as shown in FIGS. 5A, 5B. A suitable method is selected according to a measurement target selected by the examiner via the operation portion 8.

In the present embodiment, when the angle analysis is selected as the measurement target, the calculator 26 of the controller 3 adopts the radial scan as the scanning pattern. Specifically, the calculator 26 scans the 2D tomographic images of the respective sliced surfaces with a radial direction whose center is the corneal apex of the subjected eye E as a B-scan direction, and a circumferential direction of a surface of the anterior eye Ec of the subjected eye E as a C-scan direction. Hereinbelow, explanation will be given on the premise that each of the 2D tomographic images of the respective sliced surfaces which are scanned as above and stored in the storage 10 includes two positions of the angle of the anterior eye E.

<Anterior Eye 3D Image Processing (First Embodiment)>

Figure 6:
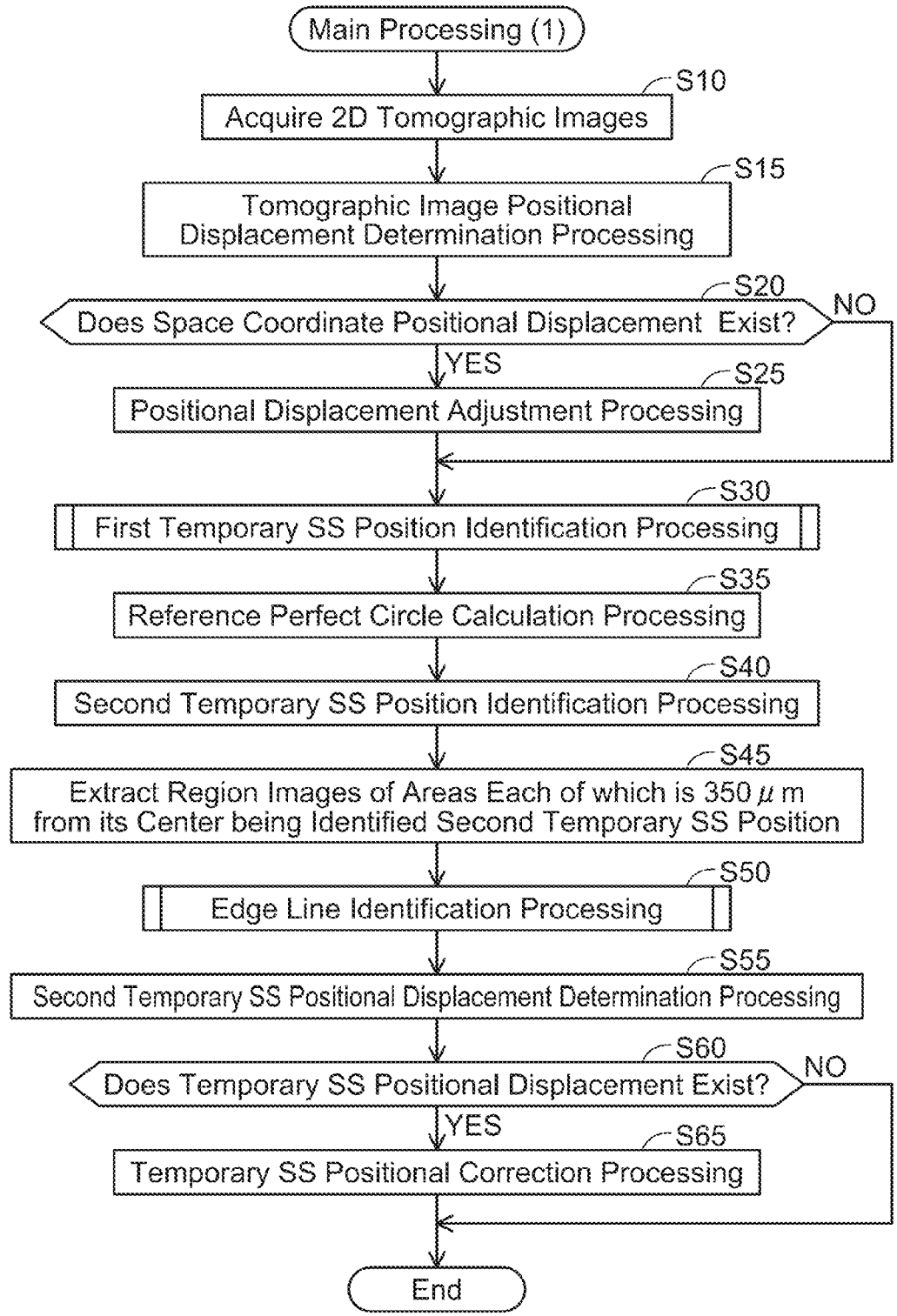
FIG. 6 is a flowchart for explaining an anterior eye three-dimensional image processing (main processing) performed by an image processor in a first embodiment.

The image processor 100 comprises the microcomputer including the CPU, the memory, and the like. The program for realizing a main function as the anterior eye 3D image processing apparatus is stored in the memory or the storage 10. The CPU executes a main processing of an anterior eye 3D image processing shown in FIG. 6 in accordance with the program.

In the main processing, in S10, the image processor 100 acquires the 2D tomographic images of the respective sliced surfaces which constitute the anterior eye 3D image from the storage 10. The respective sliced surfaces are set in advance such that a predetermined angle in the C-scan direction of the radial scan is formed between the sliced surfaces adjacent to each other based on an optical axis of the measurement light.

In the present embodiment, the predetermined angle is set at 11.25 degrees. That is, that makes thirty-two B-scan directions, and thus sixteen 2D tomographic images are acquired.

Next, in S15, the image processor 100 performs a tomographic image positional displacement determination processing. The tomographic image positional displacement determination processing is a processing that determines whether a displacement of a space coordinate position (hereafter "space coordinate positional displacement") exists or not in each of the sixteen 2D tomographic images of the respective sliced surfaces acquired in S10.

In the tomographic image positional displacement determination processing, the determination is made by using the alignment information stored in the storage 10 as well as according to whether an after-mentioned displacement of a corneal front surface curved line exists or not (or, whether the displacement is large or not) between the 2D tomographic images.

For example, for each of the 2D tomographic images of the respective sliced surfaces, based on the corresponding alignment information stored in the storage 10, in a case where at least one of its positional displacement amounts ΔX, ΔY, and ΔZ exceeds a predetermined allowable threshold, it is determined that the space coordinate positional displacement exists in the 2D tomographic image. In a case where all of the positional displacement amounts ΔX, ΔY, and ΔZ are equal to or less than the allowable thresholds, the determination of the displacement of the corneal front surface curved line relative to the threshold is made.

Then, in a case where it is determined that the displacement of the corneal front surface curved line exists, it is determined that the space coordinate positional displacement also exists. In a case where it is determined that the displacement of the corneal front surface curved line does not exist, it is determined that the space coordinate positional displacement does not exist either.

As above, in the present embodiment, both of the method in which the determination is made by using the alignment information, and the method in which the determination is made according to the displacement of the corneal front surface curved line are used. However, only one of the methods may be used.

Next, in S20, the image processor 100 bifurcates the processing according to the determination result in S15. In the case where it was determined in S15 that the space coordinate positional displacement exists, in S20 the processing proceeds to S25. In the case where it was determined in S15 that the space coordinate positional displacement does not exist, in S20 the processing proceeds to S30.

In S25, a positional displacement adjustment processing is performed. The positional displacement adjustment processing is a processing where, relative to each 2D tomographic image determined as having the space coordinate positional displacement in S15, the space coordinate positional displacement is adjusted. In the positional displacement adjustment processing of the present embodiment, relative to the positional displacement amounts $\Delta X$, $\Delta Y$, and $\Delta Z$ based on the alignment information, an offset amount $\Delta X'$ which satisfies the following formula (1) for example is found.

Figure 7A:
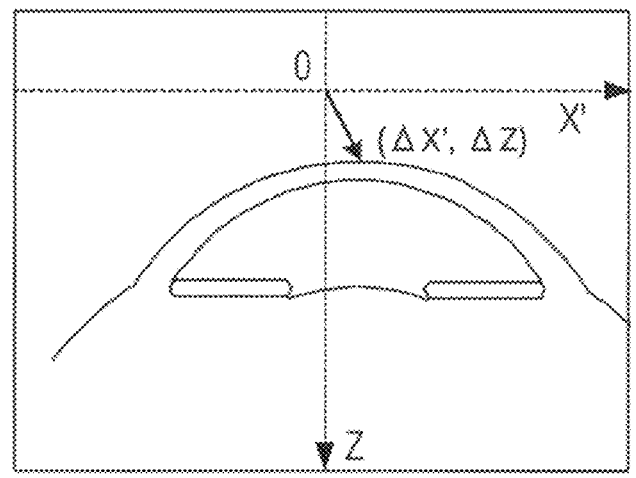
FIG. 7A is a complementary diagram for explanation of a displacement adjusting processing in the first embodiment.
Figure 7B:
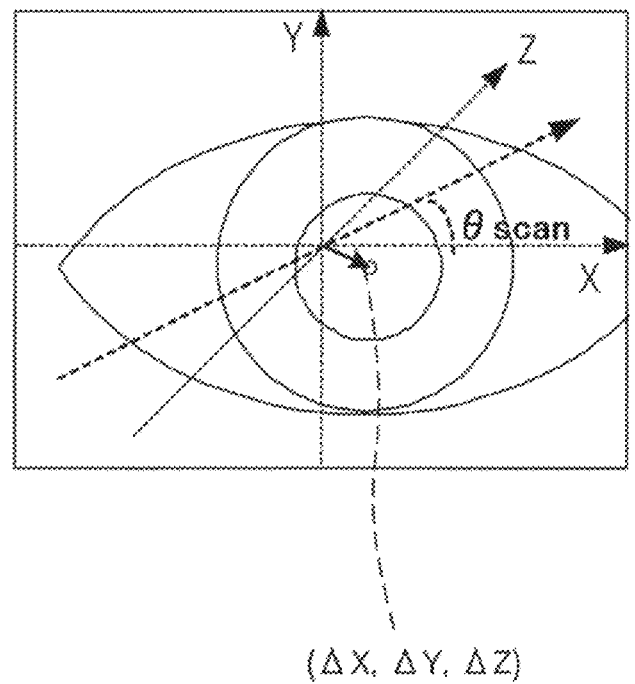
FIG. 7B is a complementary diagram for explanation of the displacement adjusting processing in the first embodiment.

Here, an offset amount of a space coordinate position in a 2D tomographic image is set as $\Delta X'$, $\Delta Z$. As shown in FIG. 7A, in a case where a direction perpendicular to the Z direction in the 2D tomographic image is termed an X' direction, the offset amount $\Delta X'$ is a correction amount of the space coordinate position in the X' direction. Further, as shown in FIG. 7B, a $\theta$ scan is an angle between the X direction and the B-scan direction of the radial scan.

[Formula 1]

$$\Delta X' = (\Delta X^2 + \Delta Y^2)^{-1/2} \times \cos(\tan^{-1}(\Delta Y/\Delta X) - \theta \text{ scan}) \quad (1)$$

The formula (1) may be used as an approximate formula in a case where the offset amount $\Delta X'$ is minute (for example, 300 µm or less). Further, in this positional displacement adjustment processing, in addition to the adjustment (correction) by using the alignment information stored in the storage 10 as above, the after-mentioned displacement of the corneal front surface curved line between the 2D tomographic images is corrected as well (see a second embodiment).

In S25, the positional displacement adjustment processing is performed to all of the 2D tomographic images stored in the storage 10, as a result of which the space coordinate positions of the respective 2D tomographic images are put together with each other and the anterior eye 3D image is restructured.

In the present embodiment, as mentioned above, both of the method in which the correction is made by using the alignment information, and the method in which the correction is made according to the displacement of the corneal front surface curved line are used. However, only one of the methods may be used. It should be however noted that, by using both methods, the positional displacement adjustment processing can be performed while complementing errors of different properties. For example, in the method in which the correction is made by using the alignment information, there is a possibility that an error occurs due to not being able to consider a rotation movement of the subjected eye E (eyeball). In the method in which the displacement of the corneal front surface curved line is corrected, there is a possibility that an error occurs in a case where the eyeball moves largely. By using both methods, the errors of different properties can be complemented.

Next, in S30, the image processor 100 selects four 2D tomographic images as representative images from among the sixteen 2D tomographic images of the respective sliced surfaces acquired in S10. Then, for each representative image, the image processor 100 performs a processing (hereinbelow referred to as "first temporary SS position identification processing") that identifies two temporary SS positions (hereinbelow, referred to as "first temporary SS positions") each of which shows a space coordinate position of a scleral spur of the anterior eye Ec.

The image processor 100 identifies eight temporary SS positions from the four representative images. In the present embodiment, the image processor 100 selects four 2D tomographic images having sliced surfaces which make an angle equal to or greater than a predetermined angle (for example, 30 degrees) relative to each other as the four representative images.

Figure 9A:
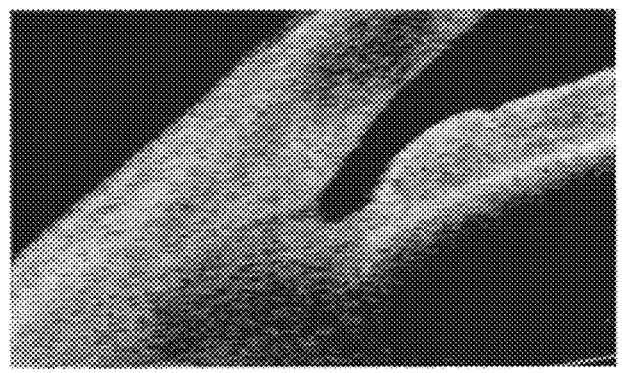
FIG. 9A is a complementary diagram for explanation of the first temporary SS position identification processing /an edge line identification processing.

FIG. 8 shows a processing content of the first temporary SS position identification processing in S30. As shown in FIG. 8, in S110, the image processor 100 extracts images including locally vicinities of the angle of the anterior eye Ec (hereinbelow referred to as "local image(s)", see FIG. 9A) from the representative images.

In S120, the image processor 100 performs a processing (hereinbelow referred to as "edge line identification processing") that identifies edge lines defining respective parts of the anterior eye Ec in the local images extracted in S110.

Figure 10:
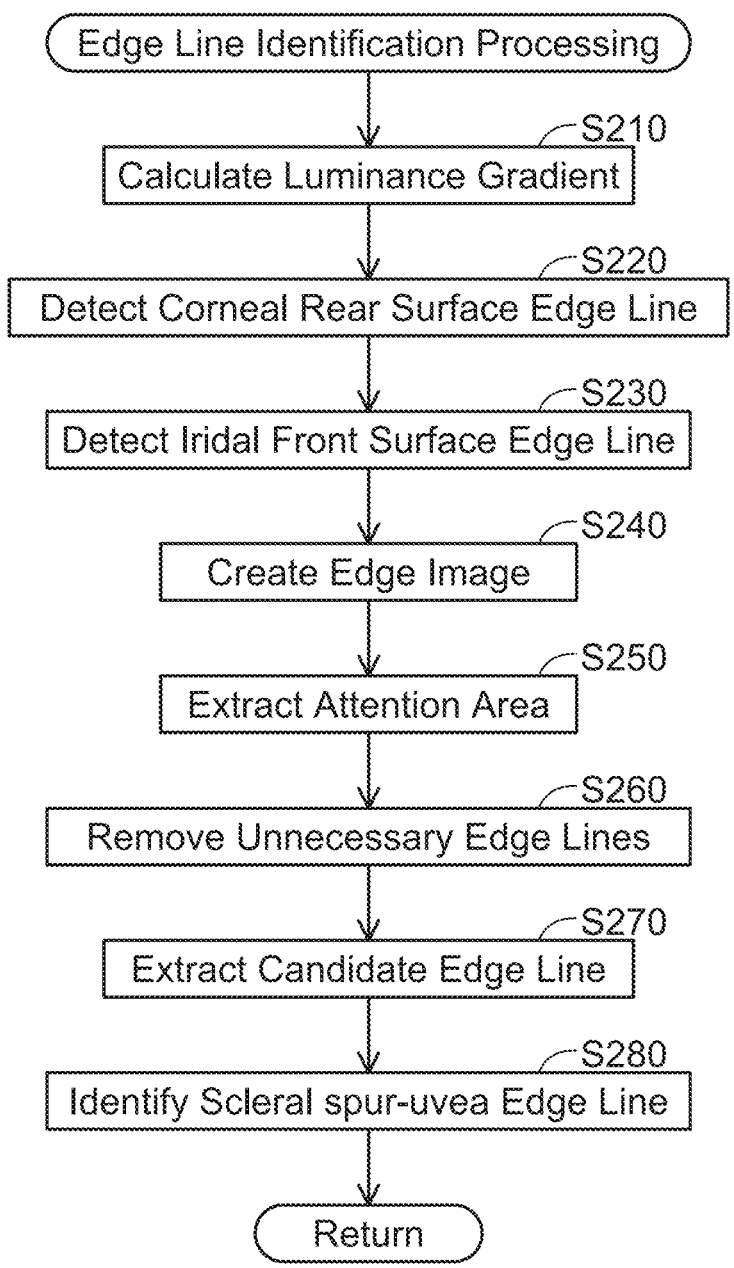
FIG. 10 is a flowchart for explaining the edge line identification processing.

FIG. 10 shows a processing content of the edge line identification processing in S120. As shown in FIG. 10, in S210, the image processor 100 calculates a luminance gradient for respective pixels in image data of the local images extracted in S110 by, for example, finding a luminance difference or the like between pixels adjacent in the Z direction.

Next, in S220, based on the luminance gradient of each local image, the image processor 100 detects an edge line indicating a corneal rear surface (hereinbelow referred to as "corneal rear surface edge line") in the anterior eye Ec. Then, in S230, the image processor 100 detects an edge line indicating an iridal front surface (hereinbelow referred to as "iridal front surface edge line") in the anterior eye Ec.

In the image data of each local image, the luminance gradient of pixels on the corneal rear surface edge line and the iridal front surface edge line is the highest. Due to this, for example, by setting an appropriate threshold for the luminance gradient, the corneal rear surface edge line and the iridal front surface edge line can be extracted (detected) from the local image.

Figure 9B:
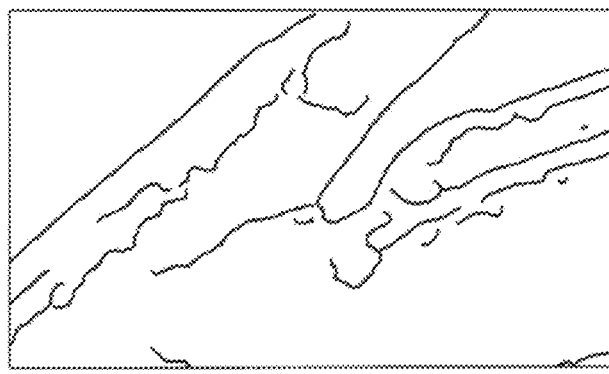
FIG. 9B is a complementary diagram for explanation of the first temporary SS position identification processing /the edge line identification processing.

Next, in S240, the image processor 100 creates images including edge lines which may possibly define respective parts in the anterior eye Ec other than the corneal rear surface edge line detected in S220 and the iridal front surface edge line detected in S230 (hereinbelow referred to as "edge images", see FIG. 9B) by variably setting the threshold for the luminance gradient in the image data of each local image.

Then, in S250, the image processor 100 extracts an attention area which is presumed to include an SS position on the corneal rear surface edge line detected in S220 from each edge image.

For example, in S250, in a case where the iridal front surface edge line could be detected in S230, the image processor 100 limits the attention area from the edge image based on a curved point of an edge line formed by connecting the two edge lines, i.e., the corneal rear surface edge line and the iridal front surface edge line (the curved point corresponding to a bottom of the angle of the anterior eye Ec).

Figure 9C:
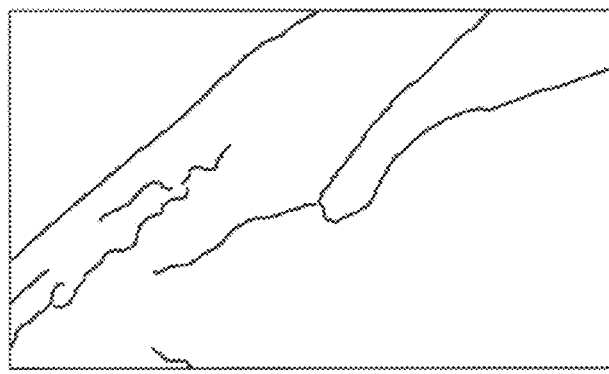
FIG. 9C is a complementary diagram for explanation of the first temporary SS position identification processing /the edge line identification processing.
Figure 9D:
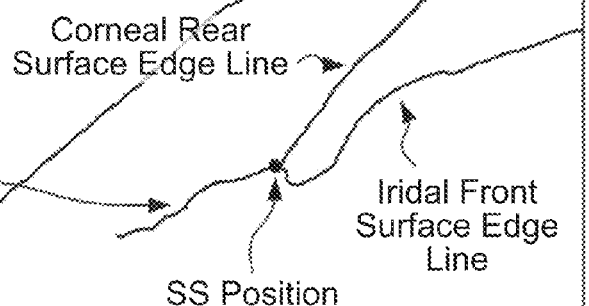
FIG. 9D is a complementary diagram for explanation of the first temporary SS position identification processing /the edge line identification processing.

Then, in S260, the image processor 100 removes edge lines generated in S240 and situated outside of the attention area extracted in S250 as unnecessary edge lines from each edge image. For example, unnecessary edge lines diverging from the corneal rear surface edge line outside of the attention area and unnecessary edge lines diverging from the iridal front surface edge line outside of the attention area are removed (see FIG. 9C).

In S270, by means of the removal of the unnecessary edge lines in S260, the image processor 100 extracts a candidate edge line which is a candidate for an edge line (hereinbelow referred to as "scleral spur-uvea edge line") indicating a boundary between the scleral spur and the uvea of the anterior eye Ec.

Next, in S280, the image processor 100 calculates magnitudes of the luminance gradient (edge strengths) for the respective candidate edge lines extracted in S270, and identifies an edge line having a largest luminance gradient among the candidate edge lines as the scleral spur-uvea edge line.

Returning to the first temporary SS position identification processing in FIG. 8, in S130, the image processor 100 determines whether the iridal front surface edge line was detected or not in S230, and bifurcates the processing according to the determination result. That is, there may be a case where the subjected eye E has a closed angle. In such case, there may be a case where the iridal front surface edge line can be integrally projected with the corneal rear surface edge line, and hence the iridal front surface edge line is not detected.

Here, in a case where the image processor 100 determines that the iridal front surface edge line could be detected, the processing proceeds to S140. In a case where the image processor 100 determines that the iridal front surface edge line could not be detected, the processing proceeds to S150.

In S140, the image processor 100 identifies as an first temporary SS position a space coordinate position indicating an intersection point of the scleral spur-uvea edge line identified in S280, the corneal rear surface edge line detected in S220, and the iridal front surface edge line detected in S230. Then, the processing proceeds to S160.

On the other hand, in S150, the image processor 100 identifies as the first temporary SS position a space coordinate position indicating an intersection point of the scleral spur-uvea edge line identified in S280 and the corneal rear surface edge line detected in S220. For example, several methods may be adopted as method of identifying the intersection point of the scleral spur-uvea edge line and the corneal rear surface edge line (that is, the first temporary SS position).

In an example, the image processor 100 may identify the first temporary SS position based on a shape of an edge line (hereinbelow referred to as "target edge line") formed by connecting the scleral spur-uvea edge line and the corneal rear surface edge line. By utilizing a fact that a slope of the scleral spur-uvea edge line is different from that of the corneal rear surface edge line in each edge image, the image processor 100 may identify as the first temporary SS position a point (curved point) at which the slope of the target edge line significantly changes so as to curve, for example.

Further, for example, the image processor 100 may identify the first temporary SS position based on information of luminance gradient on the target edge line. That is, by utilizing a fact that the luminance gradient on the corneal rear surface edge line is higher than that on the scleral spur-uvea edge line in each edge image, the image processor 100 may identify as the first temporary SS position a point on the target edge line at which the luminance gradient significantly changes, for example. Notably, in the present embodiment, the first temporary SS position is identified based on two or more edge lines, however, the first temporary SS position may be identified based on one edge line. For example, if only an image of a corneal region and anterior camber is extracted, by only using the corneal rear surface edge line, the image processor 100 may identify as the first temporary SS position an end point of the corneal rear surface edge line.

In S160, the image processor 100 determines whether or not a predetermined number of first temporary SS positions (in the present embodiment, two first temporary SS positions) could be identified in each representative image (in the present embodiment, each of the four representative images). In a case where all of the first temporary SS positions (in the present embodiment, a total of eight first temporary SS positions) could be identified, the processing returns to the main processing (S35). In a case where there is an unidentified first temporary SS position(s) in any one or more of the representative images, the processing returns to S110 and continues the first temporary SS position identification processing.

Figure 11:
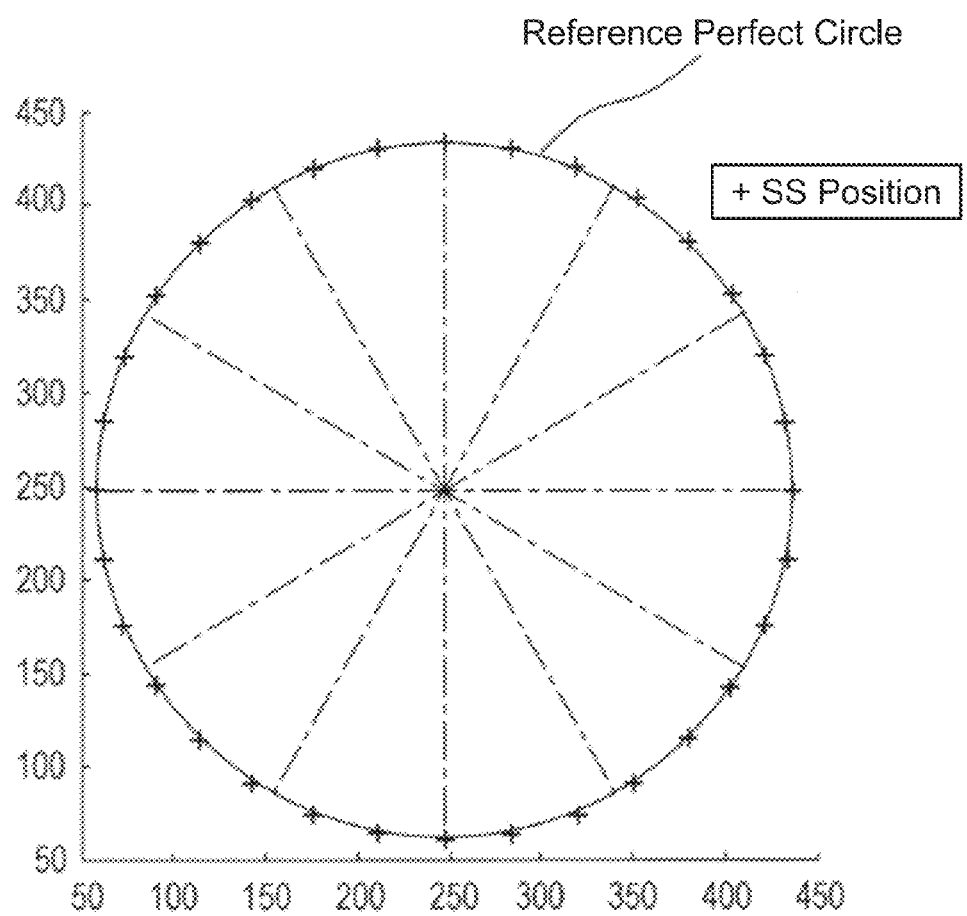
FIG. 11 is a complementary diagram for explanation of a calculation of a reference perfect circle and a second temporary SS position identification processing performed in the main processing.

When the processing returns to the main processing (S35), the image processor 100 calculates a function that shows a reference perfect circle (see FIG. 11) passing through at least three first temporary SS positions among the plurality (in the present embodiment, eight) of first temporary SS positions identified in S30 on space coordinates. Specifically, in the present embodiment, a reference perfect circle on a space plane which passes through at least three first temporary SS positions among the eight first temporary SS positions, and has minimum distances to the remaining first temporary SS positions (in other words, the remaining first temporary SS positions are positioned so as to be closest to the reference circle shown by the function) is found.

By finding the reference perfect circle such that the remaining first temporary SS positions among the eight first temporary SS positions are positioned closest to the reference perfect circle as above, errors of first temporary SS positions between the images can be appropriately dispersed, and hence accuracy in automatic identification of first temporary SS positions can be improved. In the present embodiment, a completely perfect circle is adopted as the reference perfect circle.

In S40, the image processor 100 performs a processing (hereinbelow referred to as "second temporary SS position identification processing") that identifies, based on the function of the reference perfect circle calculated in S35, temporary SS positions (hereinbelow, referred to as "second temporary SS positions") in the plurality (in the present embodiment, twelve) of 2D tomographic images other than the four representative images (hereinbelow referred to as "non-representative images") among the plurality (in the present embodiment, sixteen) of 2D tomographic images constituting the anterior eye 3D image.

Specifically, the image processor 100 identifies, on the reference perfect circle found in S35, points corresponding to the B-scan direction in each of the non-representative images as second temporary SS positions of each non-representative image.

In S45, the image processor 100 extracts, from each non-representative image, images (hereinbelow referred to as "region image(s)") of areas each of which extends 350 µm from its center that is the corresponding second temporary SS position identified in S40. The extracted image range may be equal to or less than 350 µm.

By limiting the extracted image range to the areas in the predetermined range (equal to or less than 350 µm) whose centers are the identified second temporary SS positions, it is possible to reduce detection of a wrong tissue boundary, carry out an after-mentioned arithmetic processing for correction of the second temporary SS positions at a faster speed, and improve an arithmetic accuracy.

Next, in S50, the image processor 100 performs a processing (hereinbelow referred to as "edge line identification processing") that identifies edge lines defining the respective parts of the anterior eye Ec in each of the region images extracted in S45. A content of this edge line identification processing of S50 is similar to the edge line identification processing of S120, and hence description thereof will be omitted.

Next, in S55, the image processor 100 performs a second temporary SS positional displacement determination processing. The second temporary SS positional displacement determination processing is a processing that determines whether a displacement between an expected SS position (hereinbelow referred to as "a third temporary SS position") based on the edge lines identified in S50 and the corresponding second temporary SS position identified in S40 exists or not. The expected SS position (third temporary SS position) based on the edge lines identified in S50 is, for example, a position indicating an intersection point of the scleral spur-uvea edge line and the corneal rear surface edge line that are identified in S50.

Notably, some methods may be adopted as method of identifying the expected SS position (third temporary SS position) based on the edge lines. The method of identifying the intersection point of the scleral spur-uvea edge line and the corneal rear surface edge line is mentioned above, however, the image processor 100 may identify a position of an intersection point using the iridal front surface edge line in addition to the scleral spur-uvea edge line and the corneal rear surface edge line, for example. Further, by utilizing the fact that the slope of the scleral spur-uvea edge line is different from that of the corneal rear surface edge line, the image processor 100 may identify a position of a point at which a slope of an edge line (target edge line) formed by connecting the scleral spur-uvea edge line and the corneal rear surface edge line significantly changes so as to curve (curved point) may be identified. Further, by utilizing the fact that the luminance gradient on the corneal rear surface edge line is higher than that on the scleral spur-uvea edge line, the image processor 100 may identify a position of a point at which the luminance gradient of the target edge line significantly changes may be identified. Notably, by only using the corneal rear surface edge line, the end point of the corneal rear surface edge line may be identified as the third temporary SS position.

In this temporary SS positional displacement determination processing, the determination is made according to whether a displacement exists or not between the position (third temporary SS position) indicating the intersection point of the scleral spur-uvea edge line and the corneal rear surface edge line that is identified in S50, and the second temporary SS positions identified in S40.

Specifically, in a case where the position (third temporary SS position) indicating the intersection point of the scleral spur-uvea edge line and the corneal rear surface edge line that is identified in S50 differs from the corresponding second temporary SS position identified in S40, the image processor 100 determines that an temporary SS positional displacement exists. In a case where the position (third temporary SS position) indicating the intersection point of the scleral spur-uvea edge line and the corneal rear surface edge line identified in S50 coincides with the corresponding second temporary SS position identified in S40, the image processor determines that the temporary SS positional displacement does not exist.

Next, in S60, the image processor 100 bifurcates the processing according to the determination result in S55. In the case where it was determined that the temporary SS positional displacement exists in S55, the processing proceeds to S65. In the case where it was determined that the temporary SS positional displacement does not exist in S55, the main processing comes to an end.

In S65, an temporary SS positional correction processing is performed. The temporary SS positional correction processing is a processing that corrects, relative to the non-representative images that were determined as having the temporary SS positional displacements in S55, the temporary SS positional displacements thereof. In the temporary SS positional correction processing of the present embodiment, the temporary SS positions identified in S30 and S40 are corrected so as to coincide with the positions indicating the intersection points of the scleral spur-uvea edge line and the corneal rear surface edge line identified in S50. That is, the temporary SS positions identified in S30 and S40 are corrected as the positions (third temporary SS position) of the intersection points of the scleral spur-uvea edge line and the corneal rear surface edge line identified in S50 being right SS positions. Accordingly, the image processor 100 ends the main processing.

By correcting the identified temporary SS positions, the identification of the SS positions in the 2D tomographic images can be performed stably and accurately.

Figure 12:
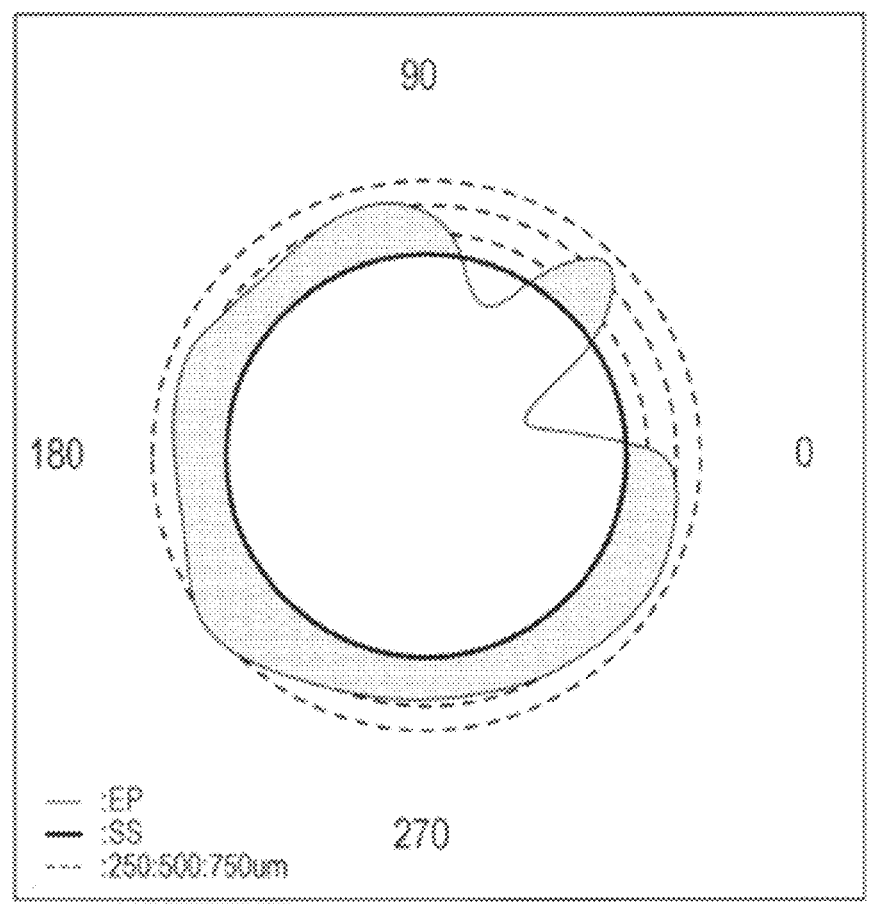
FIG. 12 is a chart exemplifying an aspect of an angle analysis (an analyzed image showing an ITC)

By using the SS positions identified for all of the sliced surfaces, the image processor 100 can create an analyzed image showing an angle portion EP (a contact portion of the corneal rear surface and the iridal front surface) which is closed beyond the SS position as an iridotrabecular contact (ITC) in a chart form (see FIG. 12). This analyzed image is outputted to the monitor 7 in accordance with operational instructions by the examiner via the operation portion 8.

Second Embodiment

Next, a second embodiment of the present disclosure will be described. Notably, the second embodiment is different from the first embodiment only in its content of the main processing (anterior eye 3D image processing) performed by the image processor 100, and hence descriptions for other contents of the second embodiment will be omitted.

Specifically, in the anterior eye 3D image processing of the first embodiment, by performing the tomographic image positional displacement adjustment processing (S25), the image processor 100 put together the space coordinate positions of the respective 2D tomographic images, and restructured the anterior eye 3D image, and then identified the SS positions in the respective 2D tomographic images constituting the restructured anterior eye 3D image (S30 to S65).

Contrary to this, the anterior eye 3D image processing of the second embodiment is different in a point that the image processor 100 determines the SS positions by using parameters calculated for adjusting displacements of the space coordinate positions of the respective 2D tomographic images without restructuring the anterior eye 3D image. This point is a difference between the first embodiment and the second embodiment. According to the anterior eye 3D image processing of the second embodiment, the image processor 100 does not restructure the anterior eye 3D image, and hence a speed of an overall processing including the angle analysis can be improved.

<Anterior Eye 3D Image Processing (Second Embodiment)>

Figure 13:
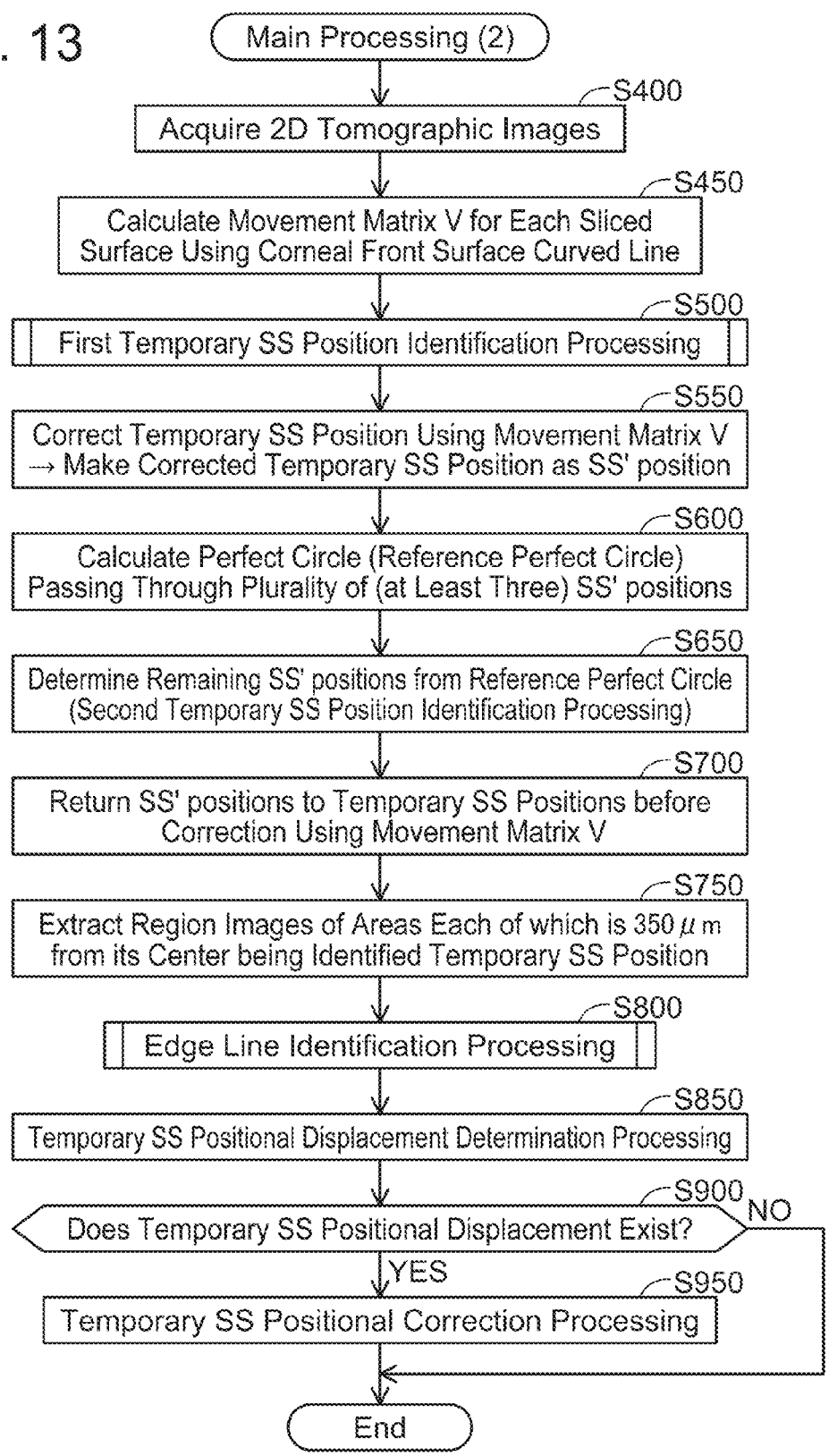
FIG. 13 is a flowchart for explaining an anterior eye three-dimensional image processing (main processing) performed by an image processor in a second embodiment.

As shown in FIG. 13, in the main processing of the second embodiment, in S400, similarly to the first embodiment, the image processor 100 acquires the 2D tomographic images of the respective sliced surfaces which constitute the anterior eye 3D image from the storage 10.

In the second embodiment, the respective sliced surfaces are set in advance such that a predetermined angle in the C-scan direction of the radial scan is formed between adjacent sliced surfaces based on the optical axis of the measurement light. In the present embodiment, the predetermined angle is set at 5.625 degrees. That is, that makes sixty four directions in the B-scan direction, and thus thirty two 2D tomographic images are acquired.

Next, in S450, the image processor 100 calculates, for each one of the thirty two 2D tomographic images of the sliced surfaces acquired in S400, a movement matrix V for aligning space coordinate positions with the adjacent 2D tomographic image of the sliced surface based on positions of their corneal front surfaces. That is, the image processor 100 calculates the corresponding movement matrix for each pair of the adjacent 2D tomographic images of the sliced surfaces.

Specifically, the image processor 100 extracts at first, a curved line indicating a shape of the corneal front surface (hereinbelow referred to as "corneal front surface curved line") from one 2D tomographic image and the adjacent one 2D tomographic image for each pair of the 2D tomographic images adjacent to each other by using a well-known technique, for example, such as a pattern matching or the like.

Figure 14:
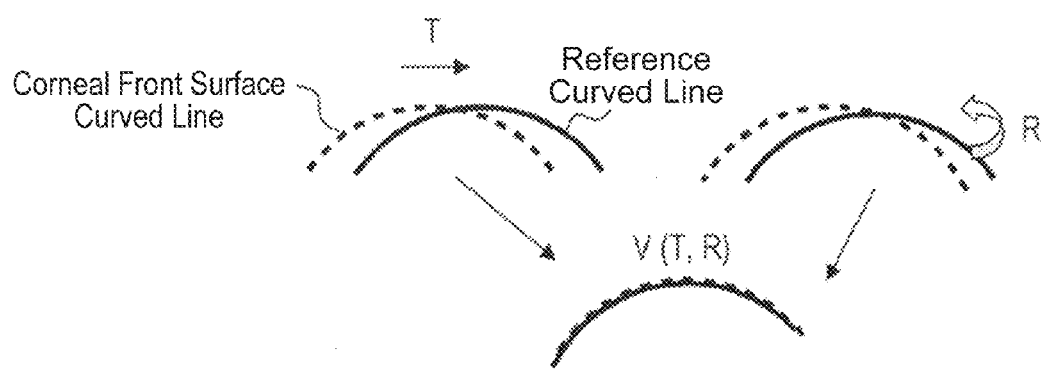
FIG. 14 is a complementary diagram for explanation of a displacement adjusting processing in the second embodiment.

Then, for example, as shown in FIG. 14, the image processor 100, for each of the extracted corneal front surface curved lines, translates and rotates one to the other side so that a reference corneal front surface curved line (hereinbelow referred to as "reference curved line") having a minimum translation distance T and rotation angle R is found. The image processor 100 calculates an input formula of the corneal front surface curved line of each 2D tomographic image whose output value is the reference curved line as a movement matrix V for each 2D tomographic image.

For example, the image processor 100 calculates movement matrixes V for all the respective 2D tomographic images, finds an average reference curved line relative to all of the 2D tomographic images, and based on this average reference curved line, corrects the movement matrixes V of the respective 2D tomographic images. Each of the movement matrixes V calculated as such is associated with the corresponding 2D tomographic image of the sliced surface and temporarily stored in the memory.

In this S450, the image processor 100 determines whether a displacement between the adjacent corneal front surface curved lines for all the 2D tomographic images exists or not (or, whether the displacement is large or not). The image processor 100 calculates the movement matrixes V in a case where the displacement between the adjacent corneal front surface curved lines exists.

Next, in S500, the image processor 100 selects three 2D tomographic images as representative images from the thirty two 2D tomographic images of the sliced surfaces which were acquired in S400 and the movement matrixes V were calculated for. The image processor 100 performs a processing (first temporary SS position identification processing) that identifies two first temporary SS positions indicating space coordinate positions of the scleral spur of the anterior eye Ec in each representative image.

In the second embodiment, the image processor 100 identifies six first temporary SS positions from the three representative images. The image processor 100 selects, as the three representative images, three 2D tomographic images sliced surfaces of which form an angle which is equal to or greater than a predetermined angle (for example, 45 degrees) relative to each other. A content of this first temporary SS position identification processing in this S500 is similar to that of the first embodiment, and hence description thereof will be omitted.

In S550, the image processor 100 adjusts (corrects) space coordinate positions of the plurality (in the present embodiment, six) of the first temporary SS positions identified in S500 (the first temporary SS position identification processing) by using the corresponding movement matrixes V calculated in S450. Notably, hereinbelow, the temporary SS positions corrected by using the movement matrixes V will referred to as "first SS' positions".

In S600, the image processor 100 calculates a function that shows a reference perfect circle (see FIG. 11) on the space coordinates which passes through at least three first SS' positions among the plurality (in the present embodiment, six) of first temporary SS positions corrected in S550.

Specifically, in the second embodiment, a reference perfect circle on the space plane which has a diameter that is a distance between two first SS' positions identified in one representative image and passes through at least one more remaining first SS' position among the remaining first SS' position(s) is found. In this case, the reference perfect circle on the space plane is set by identifying only at least one first SS' position other than the two first SS' positions constituting the diameter.

Due to this, a number of the 2D tomographic images (the representative images) used for finding the reference perfect circle can be reduced. Accordingly, more processes can be automatized.

In S650, the image processor 100 performs a processing (second temporary SS position identification processing) that identifies second SS' positions for the plurality (in the present embodiment, twenty nine) of 2D tomographic images (hereinbelow referred to as "non-representative images") other than the three representative images among the plurality (in the present embodiment, thirty two) of 2D tomographic images constituting the anterior eye 3D image based on the function of the reference perfect circle calculated in S600. Specifically, the image processor 100 identifies on the reference perfect circle found in S600, points corresponding to the B-scan direction in the respective non-representative images as second SS' positions of the non-representative images.

In S700, the image processor 100 calculates (identifies) the temporary SS positions in all of the 2D tomographic images by returning the second SS' positions of all of the 2D tomographic images identified as above to the temporary SS positions before the correction by using the corresponding movement matrixes V calculated in S450.

Then, in S750, the image processor 100 extracts, from each non-representative image, images (hereinbelow referred to as "region image(s)") of areas each of which extends 350 µm from its center that is the corresponding temporary SS position identified in S700.

Next, in S800, the image processor 100 performs a processing (hereinbelow referred to as "edge line identification processing") that identifies edge lines defining the respective parts of the anterior eye Ec in each of the region images extracted in S750. A content of this edge line identification processing is similar to that of the first embodiment, and hence explanation thereof will be omitted.

Next, in S850, the image processor 100 performs an temporary SS positional displacement determination processing. A content of this temporary SS positional displacement determination processing is similar to that of the first embodiment, and hence explanation thereof will be omitted.

Next, in S900, the image processor 100 bifurcates the processing according to the determination result in S850. In a case where it was determined that a temporary SS positional displacement exists in S850, the image processor 100 proceeds to S950. In a case where it was determined that a temporary SS positional displacement does not exist in S850, the image processor 100 ends the main processing.

In S950, a temporary SS positional correction processing is performed. A content of this temporary SS positional correction processing is similar to that of the first embodiment, and hence explanation thereof will be omitted. Accordingly, the image processor 100 ends the main processing.

<Major Effects>

As described above, in the main processing, by using two or more representative images among the 2D tomographic images which have undergone the determination on the presence or absence of the space coordinate positional displacement (for example, S10 to S15), the anterior eye OCT 1 automatically accepts the identification of three or more temporary SS positions (for example, S30), and calculates the function that shows the reference perfect circle which passes through at least three temporary SS positions on the space coordinates (for example, S35). Then, the anterior eye OCT 1 identifies the temporary SS positions (remaining temporary SS positions) in the 2D tomographic images other than the representative images (the non-representative images) based on the function of the reference perfect circle (for example, S40).

Due to this, according to the anterior eye OCT 1, the examiner does not need to input the temporary SS positions point by point at all, and thus time taken until a start of creating the chart showing the ITC can be drastically reduced, for example. Therefore, the anterior eye OCT 1 can be effectively used in clinical practice by automatizing all processes of the angle analysis using the anterior eye OCT 1.

Further, in the main processing, the anterior eye OCT 1 extracts the region images of the predetermined range with the identified temporary SS positions (for example, S30, S40) as the centers (for example, S45), and determines whether the identified temporary SS positions have a displacement or not (for example, S55 to S65).

Due to this, according to the anterior eye OCT 1, by correcting the displacements of the identified temporary SS positions, the identification of the SS positions in the 2D tomographic images can be performed stably and accurately. Further, by limiting the detection of tissue boundaries to the region images of the predetermined range with the identified temporary SS positions as the centers, detection of wrong tissue boundaries can be reduced, and the arithmetic processing for the temporary SS positional correction can be performed at a faster speed.

Other Embodiments

The first and second embodiments of the present disclosure have been described, however, it should be understood that the present disclosure is not limited to these embodiments, and the present disclosure can be achieved in various aspects within the scope which does not depart from the spirit of the present disclosure.

For example, in the aforementioned embodiments, the first temporary SS positions are automatically identified by performing the first temporary SS position identification processing in the anterior eye 3D image processing (the main processing), however, the first temporary SS position identification may be performed through an point-by-point input of first temporary SS positions by the examiner via the operation portion 8.

Further, in the aforementioned embodiments, the region images of the predetermined range in the non-representative images are extracted in the anterior eye 3D image processing (the main processing), however, region images of the predetermined range may be extracted from the representative images in addition to the non-representative images, and then the determination on the presence or absence of the displacements of the identified first temporary SS positions may be made.

Further, in the aforementioned embodiments, the first temporary SS positions are automatically identified by the reference perfect circle (completely perfect circle), however, the reference perfect circle may not necessarily be a perfect circle. For example, an ellipse may be adopted. In this case, at least five first temporary SS positions may be identified in the representative images.

Further, in the aforementioned second embodiment, in the anterior eye 3D image processing (the main processing), after the temporary SS positions have been corrected by using the corneal front surface curved lines and all of the SS' positions have been identified (S450, S550), the SS' positions are returned to the temporary SS positions before the correction (S700). However, this procedure may not necessarily be followed. For example, by performing the correction of the temporary SS positions using the corneal front surface curved lines to all of the 2D tomographic images stored in the storage 10, the space coordinate positions of the respective images may be put together and the anterior eye 3D image may be restructured.

Notably, in the aforementioned embodiments, the controller 3 stores in the storage 10 the 2D tomographic images of the respective sliced surfaces constituting the anterior eye 3D image. However, the storage 10 may store the 2D tomographic images in a server on the internet, for example.

Further, in the aforementioned embodiments, the controller 3 and the image processor 100 are configured separately in the anterior eye OCT 1, however, the controller 3 and the image processor 100 may be configured integrally. Further, the controller 3 may be configured to perform the processing performed by the image processor 100, and the image processor 100 may be configured to perform the processing performed by the controller 3.

Further, another apparatus comprising the image processor 100 may be provided separately from the anterior eye OCT 1. This apparatus may be configured to perform various kinds of processing by being connected so as to be communicable between the anterior eye OCT 1 and the server.

Further, a program causing this apparatus comprising the image processor 100 to execute the various kinds of processing may be stored in the storage 10 or the server, and the image processor 100 may load the program and execute the various kinds of processing.

What is claimed is:

1. An anterior eye three-dimensional (3D) image processing apparatus configured to process an anterior eye 3D image of a subjected eye acquired by using an optical coherence tomographic image capturing apparatus, the anterior eye 3D image processing apparatus comprising:
   a processor; and
   a memory storing computer-readable instructions therein, the computer-readable instructions, when executed by the processor, causing the anterior eye 3D image processing apparatus to perform:
   acquiring a plurality of two-dimensional (2D) tomographic images constituting the anterior eye 3D image;
   identifying first temporary SS positions in each of at least two representative images selected from the plurality of 2D tomographic images, each of the first temporary SS positions indicating a space coordinate position of a scleral spur of the subjected eye;
   calculating a reference circle passing through at least three of the first temporary SS positions in the anterior eye 3D image;
   identifying second temporary SS positions in each of at least one non-representative image by using the calculated reference circle on a presumption that the scleral spur is located on the calculated reference circle, the at least one non-representative image being other than the at least two representative images among the plurality of 2D tomographic images;
   extracting regions in a predetermined range in each of at least one 2D tomographic image selected from the at least two representative images and the at least one non-representative image, in a case where the at least one 2D tomographic image selected from the at least two representative images, each of the regions being centered at a corresponding one of the identified first temporary SS positions, in a case where the at least one 2D tomographic image selected from the at least one non-representative image, each of the regions being centered at a corresponding one of the identified second temporary SS positions;
   identifying at least one of edge lines each of which indicating a tissue boundary that exists in each of the extracted regions; and
   correcting the identified first temporary SS positions or the second temporary SS positions based on the identified at least one of the edge lines.

2. The anterior eye 3D image processing apparatus according to claim 1, wherein the identified at least one of the edge lines comprise a scleral spur-uvea edge line indicating a boundary between the scleral spur and an uvea, and a corneal rear surface edge line indicating a rear surface of a cornea.

3. The anterior eye 3D image processing apparatus according to claim 1, wherein when the identified first temporary SS positions or the second temporary SS positions are different from third temporary SS positions which are identified as positions of the scleral spur based on the identified edge lines, the third temporary SS positions are identified as SS positions.

4. The anterior eye 3D image processing apparatus according to claim 3, wherein each of the third temporary SS positions is a position of an intersection point of the scleral spur-uvea edge line indicating the boundary between the scleral spur and the uvea, and the corneal rear surface edge line indicating the rear surface of the cornea.

5. The anterior eye 3D image processing apparatus according to claim 3, wherein each of the third temporary SS positions is a position of a curved point of an edge line which is formed by connecting the scleral spur-uvea edge line indicating the boundary between the scleral spur and the uvea and the corneal rear surface edge line indicating the rear surface of the cornea.

6. The anterior eye 3D image processing apparatus according to claim 3, wherein each of the third temporary SS positions is a position that is identified based on luminance gradient information of the edge line formed by connecting the scleral spur-uvea edge line indicating the boundary between the scleral spur and the uvea and the corneal rear surface edge line indicating the rear surface of the cornea.

7. The anterior eye 3D image processing apparatus according to claim 1, wherein the predetermined range is a range that extends equal to or less than 350 μm from a center of the range that is the corresponding one of the identified first temporary SS positions or the second temporary SS positions.

8. A method of processing an anterior eye three-dimensional (3D) image of a subjected eye acquired by using an optical coherence tomographic image capturing apparatus, the method comprising:
   acquiring a plurality of two-dimensional (2D) tomographic images constituting the anterior eye 3D image;
   identifying first temporary SS positions in each of at least two representative images selected from the plurality of 2D tomographic images, each of the first temporary SS positions indicating a space coordinate position of a scleral spur of the subjected eye;
   calculating a reference circle passing through at least three of the first temporary SS positions in the anterior eye 3D image;
   identifying second temporary SS positions in each of at least one non-representative image by using the calculated reference circle on a presumption that the scleral spur is located on the calculated reference circle, the at least one non-representative image being other than the at least two representative images among the plurality of 2D tomographic images;
   extracting regions in a predetermined range in each of at least one 2D tomographic image selected from the at least two representative images and the at least one non-representative image, in a case where the at least one 2D tomographic image selected from the at least two representative images, each of the regions being centered at a corresponding one of the identified first temporary SS positions, in a case where the at least one 2D tomographic image selected from the at least one non-representative image, each of the regions being centered at a corresponding one of the identified second temporary SS positions;
   identifying at least one of edge lines each of which indicating a tissue boundary that exists in each of the extracted regions; and
   correcting the identified first temporary SS positions or the second temporary SS positions based on the identified at least one of the edge lines.

* * * * *